United States Patent [19]

Fleischmann

[11] 4,003,396

[45] * Jan. 18, 1977

[54] PROPORTIONAL CONTROL CLOSED CIRCUIT GAS ADMISSION SYSTEM

[76] Inventor: Lewis W. Fleischmann, 8502 Allenswood Road, Randallstown, Md. 21133

[*] Notice: The portion of the term of this patent subsequent to Jan. 21, 1992, has been disclaimed.

[22] Filed: Nov. 21, 1974

[21] Appl. No.: 526,057

Related U.S. Application Data

[62] Division of Ser. No. 278,725, Aug. 8, 1972, Pat. No. 3,861,412.

[52] U.S. Cl. ............................. 137/83; 137/487.5
[51] Int. Cl.² .................... A62B 7/02; F16K 31/12
[58] Field of Search ............ 137/83, 829, 831, 488, 137/487.5; 91/3; 128/142

[56] References Cited
UNITED STATES PATENTS

| | | |
|---|---|---|
| 2,903,007 | 9/1957 | Zieboltz ................................. 137/83 |
| 3,628,552 | 12/1971 | Stern .............................. 137/829 X |

FOREIGN PATENTS OR APPLICATIONS

| | | |
|---|---|---|
| 689,814 | 2/1930 | France .................................. 137/83 |
| 567,913 | 12/1932 | Germany ............................... 137/83 |
| 293,790 | 12/1932 | United Kingdom ..................... 91/3 |

*Primary Examiner*—Alan Cohan
*Attorney, Agent, or Firm*—Shapiro and Shapiro

[57] ABSTRACT

Partial pressure of oxygen in a closed gas-containing system is controlled automatically. Unique electromechanical transducers employ electric meter movements to vary the angle of a surface in a jet of gas in response to a signal from an oxygen sensor, thereby to vary the direction of the jet and the stagnation pressure in a receiver. The kinetic energy of the jet is maintained constant irrespective of ambient pressure by a constant differential pressure regulator. A pneumatically operated servo valve responsive to the stagnation pressure in the receiver controls the admission of oxygen to the system.

5 Claims, 14 Drawing Figures

SENSOR SIGNAL

PROPORTIONAL CONTROL CLOSED CIRCUIT GAS ADMISSION SYSTEM

This is a division of application Ser. no. 278,725 filed Aug. 8, 1972 now U.S. Pat.No. 3,861,412.

BACKGROUND OF THE INVENTION

This invention is concerned with the measurement and control of the partial pressure of a gas such as oxygen in gas-containing systems and is also concerned with improved transducers for use in gas flow control and other systems.

In life support systems, such as those associated with deep sea diving, exploration of outer space, and medical respiration applications, accurate measurement and control of the partial pressure of oxygen in the breathing atmosphere have been difficult to achieve, especially without undue complexity and weight. In order to overcome the disadvantages of prior systems which require amplification of the signal from an oxygen sensor in order to operate a solenoid oxygen admission valve, the applicant has previously proposed a system employing novel low-power electromechanical transducers for pneumatically controlling an oxygen admission valve directly in response to the signal output of a galvanic oxygen sensor. Such a transducer may vary the back pressure upon a servo valve controlling diaphragm by varying the gap between a jet nozzle and the periphery of a disc which is turned by an electric meter movement. When the applicant's prior system is employed in deep sea diving, for example, the flow of oxygen through the nozzle provides the diver's minimum metabolic uptake requirement, namely 0.3 standard liters per minute flow. In order to provide this low control flow through the nozzle, the gap between the nozzle and the disc must be set very close, that is, between 0.0003 and 0.001 inches. With the very small gap required for the minimum metabolic uptake, the disc may become jammed against the nozzle due to foreign particles, thermal expansion, or wear. The gap setting can be made larger, but the increase in oxygen flow can be dangerous if only one diver is breathing from the system and is resting or performing little work. The excess beyond the minimum metabolic uptake requirement could be bled to the outside of the system, but this would decrease the overall efficiency of the system and would produce escaping bubbles detrimental to convert use of the system. Moreover, the applicant's prior transducers have not been insensitive to the effects of varying ambient pressure in the system.

Electromechanical transducers proposed by others are even less satisfactory. For example, one such transducer employs the stagnation pressure produced in a receiver by a jet of gas from a nozzle. The stagnation pressure is varied by a surface which is attached to an electric meter movement and which enters the stream of gas laterally and gradually blocks the jet. Jet outlet pressures, and hence the transducer gain, are limited because of the reaction upon the surface, which is part of a long lever arm, and the power required to operate the transducer is higher than the available from low signal level sensors.

BRIEF DESCRIPTION OF THE INVENTION

It is accordingly a principal object of the present invention to provide improved apparatus for use in life support systems.

A further object of the invention is to provide improved apparatus for controlling the admission of a gas to a gas-containing system.

Another object of the invention is to provide improved apparatus for maintaining a desired partial pressure of oxygen in a life support system.

Still another object of the invention is to provide improved electro-mechanical transducers.

A further object of the invention is to provide simple high-gain electro-mechanical transducers in which very small electric signals vary the stagnation pressure produced by a jet of fluid in a receiver.

Yet another object of the invention is to provide transducers of the foregoing type in which the kinetic energy of the jet is maintained constant irrespective of the ambient pressure.

A still further object of the invention is to provide transducers of the foregoing type which can be readily adjusted to set a desired output level.

Briefly stated, as applied to a closed-circuit gas-containing system for life support, for example, a preferred embodiment of the invention may comprise an electro-mechanical transducer having a nozzle for producing a fluid jet and a receiver which receives and stagnates the jet. A taut band meter movement provides a surface which intersects the jet. When the band is twisted in response to a signal applied to the armature of the meter movement from an oxygen sensor, the jet is deflected by the band to vary the impingement of the jet upon the receiver and hence to vary the stagnation pressure in the receiver. The jet is open to the system ambient pressure, and the kinetic energy of the jet is maintained constant by a constant differential pressure regulator, irrespective of the ambient pressure. The stagnation pressure in the receiver controls a pneumatically operated valve for admitting oxygen to the system. The sensor, transducer, and valve form a closed servo-loop to maintain a desired partial pressure of oxygen in the system. The partial pressure may be set initially by turning the nozzle and the receiver manually about the axis of the taut band.

BRIEF DESCRIPTION OF THE DRAWINGS

The invention will be further described in conjunction with the accompanying drawings, which illustrate preferred and exemplary embodiments, and wherein.

DETAILED DESCRIPTION OF THE INVENTION

Figure 1:
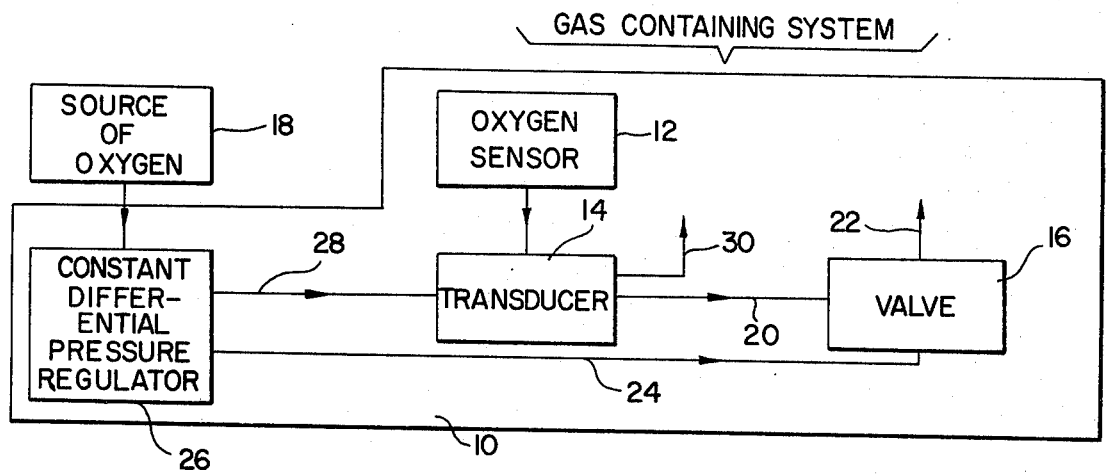
FIG. 1 is a block diagram illustrating the utilization of the invention in controlling the partial pressure of oxygen in a gas-containing system.

Referring to the drawings, and initially to FIG. 1 thereof, the invention may be employed, for example, to maintain a preset partial pressure of oxygen in a gas-containing system 10, such as a closed-circuit breathing system for deep sea diving. A galvanic oxygen sensor 12, such as a Biomarine tye OA200, produces a low level electric signal proportional to the partial pressure of oxygen in the system 10. The signal is applied to an electro-mechanical transducer 14, the mechanical output of which is in the form of a pneumatic pressure applied to operate a pilot servo valve 16, which controls the flow of oxygen to the system 10 from a source of oxygen 18. The system also contains a conventional diluent gas, such as helium or nitrogen. The pneumatic pressure applied to valve 16 is indicated by path 20, while the output from valve 16 to the system 10 is indicated by path 22. The input to valve 16 from the source of oxygen 18 is indicated by path 24 from a constant differential pressure regulator 26, such as a Wilkerson miniature regulator Model No. 2019, although the path 24 may extend directly from the oxygen source 18. The constant differential pressure regulator supplies oxygen to the transducer 14 along path 28, thereby maintaining constant the kinetic energy of a fluid jet in transducer 14 (to be described hereinafter) irrespective of the ambient pressure in the system 10. The gas flow from the jet is vented to the system 10 as indicated by path 30.

Figure 2:
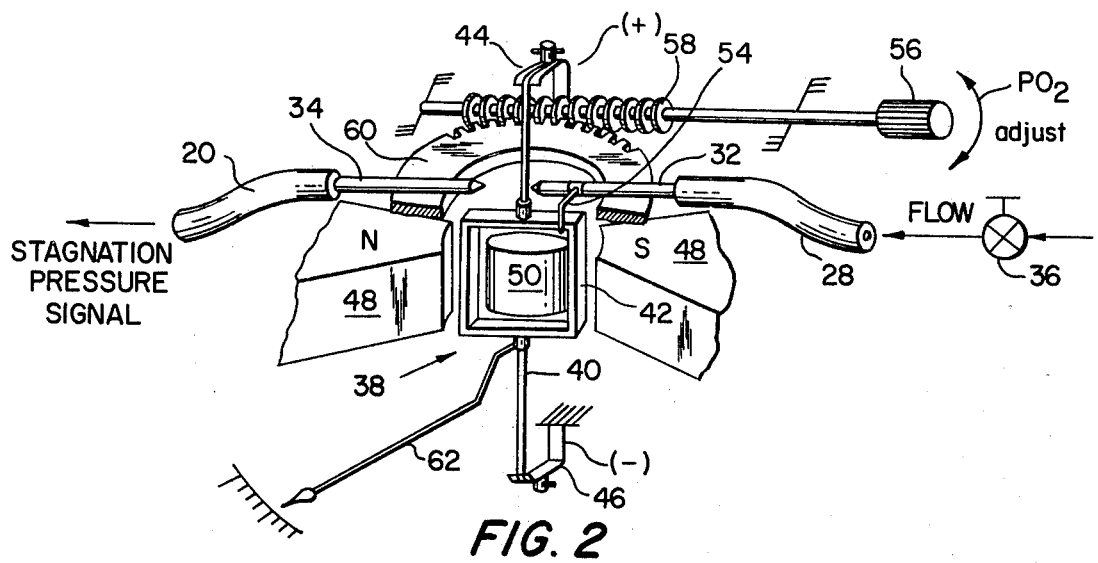
FIG. 2 is a diagrammatic perspective view of a transducer in accordance with the invention.
Figure 3A:
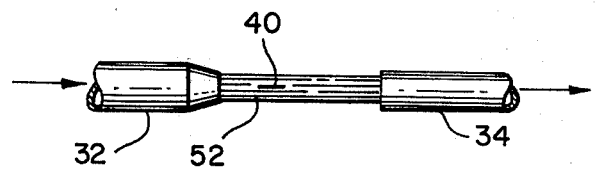
FIGS. 3a and 3b are diagrammatic views illustrating the manner in which the jet of the invention is deflected.
Figure 3B:
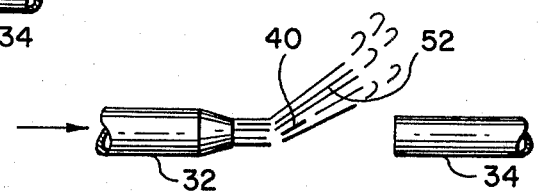

A preferred form of transducer 14 is illustrated in FIG. 2. A nozzle 32 is aligned with a tubular receiver 34, which is spaced therefrom. Oxygen from source 18 is applied to the nozzle 32 through a fixed orifice or a needle valve 36 to produce a subsonic laminar jet from the nozzle, which may be normally directed toward the receiver 34. The direction of the jet is varied by a taut band meter movement or motor 38 to vary the stagnation pressure in the receiver 34, which is connected to a closed chamber as will be described hereinafter. The basic taut band meter movement may be a Triplett Model No. 220-G, comprising a very thin, elongated, taut, resilient, metal band 40 which suspends an armature or rotor 42 between terminals 44 and 46 in the field of a permanent magnet 48 of the stator. The DC voltage from the oxygen sensor is applied between terminals 44 and 46, and current is conducted by the taut band 40 to coils wound about the sides of the rectangular armature form, which turns about a stationary soft iron core 50. The taut band 40 intersects the jet 52 near the nozzle 32 as shown in FIG. 3a. When the width of the band is parallel to the direction of the jet, as shown in FIG. 3a, the full stagnation pressure of the jet is applied to the receiver 34. When a current is applied to the armature, the taut band twists about its length, and the angle of the band surface relative to the direction of the jet flowing from the nozzle varies as shown in FIG. 3b, redirecting or deflecting the jet with respect to the receiver 34. FIG. 3b illustrates the laminar jet deflected completely away from the receiver and made turbulent by the deflection, resulting in loss of stagnation pressure in the receiver. The width of the taut band is much greater than its thickness, and the band is closer to the nozzle than to the receiver, resulting in high sensitivity.

In FIG. 2 the meter movement 38 is shown at rest, and the width of the band is assumed to be parallel to the direction of the jet from nozzle 32 throughout the length of the band. The stagnation pressure in receiver 34 is at a maximum. When the armature 42 is rotated counterclockwise by the signal from the sensor 12, the armature pulls away from a stop pin 54 which is an integral part of nozzle 32. The band 40 twists about its length (the twist being most pronounced near the armature, where the band intersects the jet), and the angle of the band surface varies relative to the axis of the nozzle 32 to change the direction of the jet and thus to reduce the stagnation pressure. This may close the oxygen supply valve, as will be seen later, so that the oxygen partial pressure will be set at a given level determined by the amount of oxygen admitted before the valve is closed. If it is desired to set a different partial pressure of oxygen, knob 56 is adjusted to turn the worm gear 58 and spur gear 60, to which the nozzle 32 and receiver 34 are fixed, for movement about the axis of the band 40. Turning gear 60 counterclockwise in FIG. 2 causes the stop pin 54 to pull the armature 42 and causes the armature and the taut band 40 to turn counterclockwise along with the nozzle and the receiver, maintaining the angle of the taut band relative to the direction of the jet from the nozzle by twisting the taut band. This applies a static restoring torque to the armature which must be overcome by the electrical signal before the armature will turn away from the stop pin 54 to reduce the stagnation pressure. Thus, the partial pressure will be higher, because the oxygen admission valve will remain open until a high enough signal is generated from the sensor to turn the armature further conterclockwise. Turning gear 60 clockwise turns the axis of nozzle 32 relative to the surface of the taut band (the stop 54 moving away from the armature), thereby reducing the stagnation pressure and tending to close the oxygen admission valve. Thus the oxygen partial pressure will be lower. Pin 54 also prevents an error signal in the event that the entire assembly is accelerated about the rotational axis (the length of the taut band) as might occur because of movement of the diver. The pointer 62, which is a part of the meter movement, is not required but can be retained to provide additional readout capability.

Figure 4:
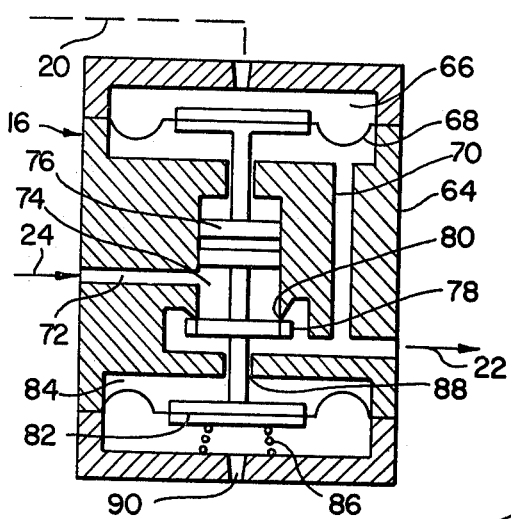
FIG. 4 is a cross-sectional view of a pneumatically operated valve which may be employed in the invention.

FIG. 4 illustrates a pneumatically actuated pilot valve 16 which may be employed in conjunction with the transducers of the invention. The valve comprises a block 64 having a chamber 66 divided by a diaphragm 68. At one side of the diaphragm the chamber is connected to path 20 from the receiver 34 of the transducer. At the other side of the diaphragm the chamber is connected by a passage 70 to path 22 (system ambient). Supply pressure along path 24 is applied to a passage 72 connected to a bore 74 containing a piston 76. One side of the piston is connected to diaphragm 68, and the other side is connected to a poppet valve 78 which engages a seat 80. The poppet valve is also connected to a diaphragm 82 which divides a chamber 84. A spring 86 in chamber 84 applies a closing bias to the poppet valve. Chamber 84 is vented to ambient at 38 and 90.

When the stagnation pressure applied along path 20 to diaphragm 68 overcomes the bias of spring 86, poppet valve 78 is unseated, permitting oxygen supplied along path 24 to be admitted to the system along path 22. The stagnation pressure is proportional to the electric signal applied to the transducer from the oxygen sensor, and as the partial pressure of the oxygen in the system builds up, the signal increases and turns the taut band so as to reduce the stagnation pressure, moving the valve so as to reduce the flow of oxygen to the system. As oxygen is consumed, the partial pressure drops, the sensor signal drops, and the stagnation pressure increases to open the valve more fully in order to admit sufficient oxygen to maintain the partial pressure constant.

Figure 5:
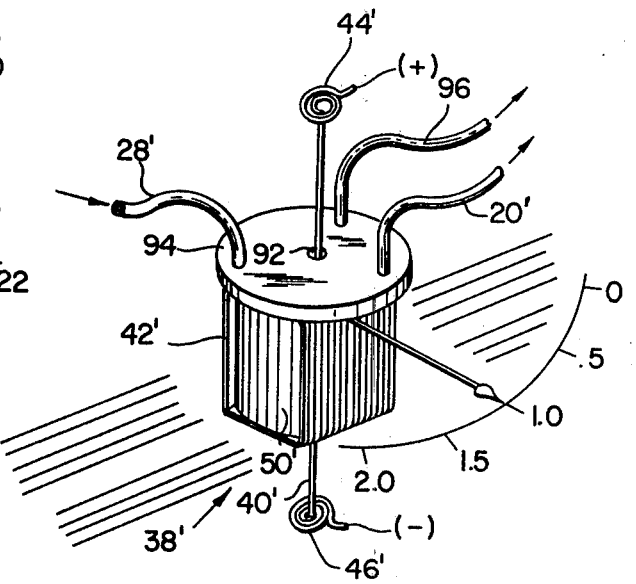
FIG. 5 is a diagrammatic perspective view of another form of transducer in accordance with the invention.
Figure 6A:
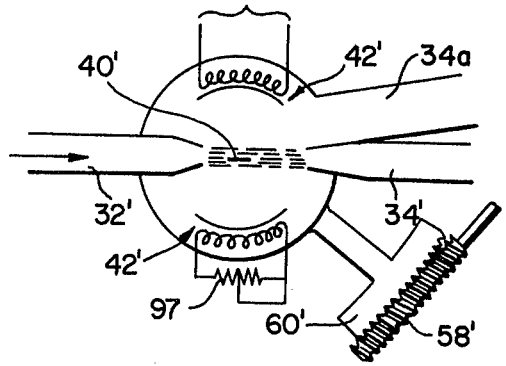
FIGS. 6a – 6c are diagrammatic views illustrating the operation of the transducer of FIG. 5.
Figure 6B:
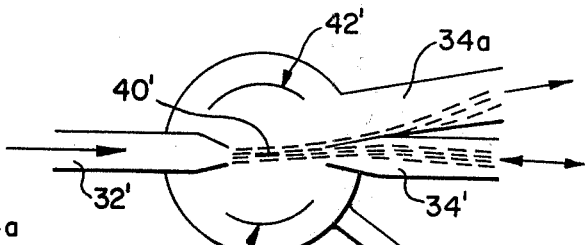
Figure 6C:
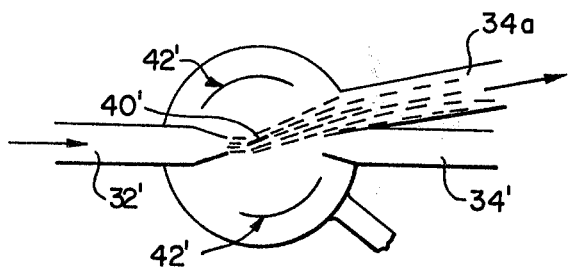

FIG. 5 illustrates a modified transducer of the invention. Primed reference characters are used in this and other modifications to designate similar parts. In this form of the invention the taut band meter movement 38' may be essentially the same as that previously described (although coil springs 44' and 46' are shown at the ends of the taut band 40'). The armature 42' rotates in the field of a permanent magnet as before and has a soft iron core 50'. The taut band 40' passes through a hole 92 (open to system ambient) in a fluid proportioning chip or disc 94 having a fluid supply pipe 28' from the constant differential pressure regulator and a pair of outlet pipes 20' (which may be connected to chamber 66 of valve 16) and 96 (which may be connected to port 90 of the valve). As shown in FIGS. 6a – 6c, the chip 94 comprises a nozzle 32' (connected to pipe 28') and a receiver 34' (connected to pipe 20'). A further receiver or vent 34a (connected to pipe 96) is adjacent to receiver 34', so that the twisting of the taut band 40' controls the proportion of the jet which impinges upon receiver 34' and receiver 34a, FIG. 6a indicating full stagnation pressure in receiver 34', FIG. 6b indicating partial stagnation pressure in receiver 34', and FIG. 6c indicating complete venting of the jet to receiver 34a. The stagnation pressure in receiver 34a assists the spring 86 in maintaining the poppet valve 78 closed. Alternatively, receiver 34a may merely be employed as a vent to the system ambient. Initial adjustment of the tension in the taut band may be accomplished by means of the worm gear 58' and spur gear 60', which turn the nozzle 32' and the receivers 34' and 34a unitarily and which may also turn the armature of the meter movement by means of stop of the type shown in FIG. 2. Potentiometer 97 shunts a portion of the armature winding and provides a vernier adjustment of partial pressure (which may be used in all embodiments).

Figure 7:
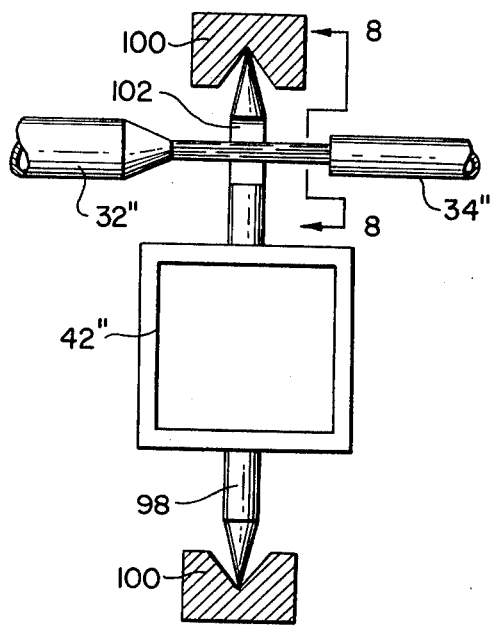
FIG. 7 is a diagrammatic vertical sectional view illustrating a further form of transducer in accordance with the invention.
Figure 8:
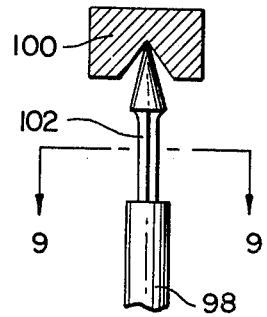
FIG. 8 is a sectional view along line 8—8 of FIG. 7.
Figure 9:
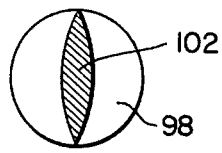
FIG. 9 is a sectional view along line 9—9 of FIG. 8.

FIG. 7 illustrates a further embodiment of the transducer, which comprises an armature 42' fixed to a shaft 98 having ends supported in jewel bearings 100. The armature rotates in the field of a permanent magnet (not shown) as before and has a soft iron core (not shown) as before. Shaft 98 is undercut to provide a vane 102 (see FIGS. 8 and 9) which may normally be aligned with the axis of nozzle 32" and the receiver 34". The shaft 98 or auxiliary conductors carry current to the armature, and coil springs (not shown) attached to shaft 98 may provide the armature restoring torque.

Figure 10:
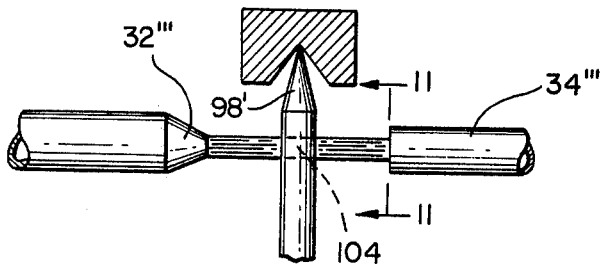
FIG. 10 is a fragmentary diagrammatic sectional view of still another transducer of the invention.
Figure 11:
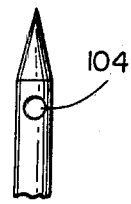
FIG. 11 is a sectional view taken along line 11—11 of FIG. 10.

FIGS. 10 and 11 illustrate a modification in which the transducer is identical to that shown in FIG. 7 except that the shaft 98' has a passage 104 through which the jet passes to receiver 34'''. As the armature turns and the orientation of the passage changes, the jet is redirected. The passage is preferably close enough to the nozzle 32''' and the passage entrance is wide enough to admit substantially the entire jet even when the passage is angulated with respect to the direction of the jet from the nozzle.

While the transducers of the invention have been described with respect to an operating mode in which an increase in stagnation pressure causes oxygen to be admitted to the system the operating mode may be reversed so that a decrease in stagnation pressures causes the admission of oxygen. This may be achieved by employing a spring to hold the admission valve open and by utilizing the stagnation pressure against the spring bias to close the valve.

It is desirable that the kinetic energy of the jet remain constant irrespective of the ambient pressure, so that the stagnation pressure varies with the signal applied to the transducer independently of the system ambient. This requires that the regulator supplying oxygen to the nozzle be a constant differential pressure type. Once set, the regulator will deliver a constant pressure greater than the ambient pressure, irrespective of the ambient pressure. As the ambient pressure increases, for example, the mass flow rate of the fluid of the jet increases linearly. The velocity of the jet decreases linearly, however, (due to increase in collisions between the molecules) so that the kinetic energy remains constant. For application to diving apparatus, the differential pressure regulator may be set to 15psig, assuring that a subsonic fluid velocity (which may be 1000 ft/sec.) will always exist at the nozzle outlet in the ambient pressures encountered in diving. The needle valve or the nozzle orifice can be sized or adjusted to deliver very small flow rates, say 0.1 standard liters per minute, at standard atmospheric pressure.

While preferred embodiments of the invention have been shown and described, it will be apparent to those skilled in the art that changes can be made in these embodiments without departing from the principles and spirit of the invention, the scope of which is defined in the appended claims.

The invention claimed is:

1. Apparatus for controlling partial pressure of a controlled gas in a gas-containing system, which comprises nozzle means for producing a jet of gas, means for providing a substantially constant pressure drop through said nozzle means irrespective of the pressure at the output of said nozzle means, means for variably interposing a surface into said jet of gas, sensor means responsive to said partial pressure in said system for adjusting said interposing means, means responsive to said jet for producing an output which varies with said interposing of said surface into said jet, and means responsive to said output for controlling the admission of controlled gas to said system.

2. Apparatus in accordance with claim 1, wherein said means for providing a substantially constant pressure drop comprises a constant differential pressure regulator between the input of said nozzle means and a source of gas for said nozzle means.

3. Apparatus in accordance with claim 1, wherein said jet is exposed to the ambient pressure of said system and wherein said means for providing a substantially constant pressure drop maintains the kinetic energy of said jet substantially constant irrespective of said ambient pressure.

4. Apparatus in accordance with claim 1, wherein said means responsive to said jet comprises receiver means spaced from said nozzle means for receiving said gas and wherein said means for interposing surface into said jet comprises means between said nozzle means and said receiver means for deflecting said jet of gas with respect to said receiver means in order to vary the impingement of said jet of gas upon said receiver means and to vary the pressure in said receiver means.

5. Apparatus in accordance with claim 1, wherein said jet is a subsonic velocity jet.

* * * * *